United States Patent
Kanda (10) Patent No.: US 8,396,271 B2
(45) Date of Patent: Mar. 12, 2013

(54) IMAGE PROCESSING APPARATUS, IMAGE PROCESSING PROGRAM RECORDING MEDIUM, AND IMAGE PROCESSING METHOD

(75) Inventor: Yamato Kanda, Tokyo (JP)

(73) Assignee: Olympus Corporation, Tokyo (JP)

( * ) Notice: Subject to any disclaimer, the term of this patent is extended or adjusted under 35 U.S.C. 154(b) by 188 days.

(21) Appl. No.: 12/959,469

(22) Filed: Dec. 3, 2010

(65) Prior Publication Data

US 2011/0069876 A1 Mar. 24, 2011

Related U.S. Application Data

(63) Continuation of application No. PCT/JP2009/060186, filed on Jun. 3, 2009.

(30) Foreign Application Priority Data

Jun. 5, 2008 (JP) ................................. 2008-147996

(51) Int. Cl.
   *G06K 9/00* (2006.01)
   *A61B 6/00* (2006.01)
(52) U.S. Cl. ......................... 382/128; 382/219; 600/476
(58) Field of Classification Search .................. 382/100, 382/107, 108, 128–134, 155, 168, 173, 181, 382/184, 190, 199, 209, 219, 232, 254, 274, 382/276, 286, 294, 305, 312, 321; 600/476, 600/178
See application file for complete search history.

(56) References Cited

U.S. PATENT DOCUMENTS

| 7,530,948 | B2 * | 5/2009 | Seibel et al. .................. 600/178 |
| 7,953,261 | B2 * | 5/2011 | Nishimura et al. ........... 382/128 |
| 8,068,897 | B1 * | 11/2011 | Gazdzinski .................... 600/476 |
| 8,107,704 | B2 * | 1/2012 | Kanda et al. .................. 382/128 |
| 2007/0165932 | A1 | 7/2007 | Nishimura et al. |
| 2009/0202117 | A1 * | 8/2009 | Vilarino et al. ............... 382/128 |
| 2009/0202124 | A1 * | 8/2009 | Matsuda et al. .............. 382/128 |

FOREIGN PATENT DOCUMENTS

| JP | 2007-175432 | 7/2007 |
| JP | 2008-093172 | 4/2008 |

OTHER PUBLICATIONS

International Search Report dated Sep. 15, 2009.

* cited by examiner

*Primary Examiner* — Seyed Azarian
(74) *Attorney, Agent, or Firm* — Scully, Scott, Murphy & Presser, P.C.

(57) ABSTRACT

An image processing apparatus includes: a category area dividing unit that divides each image constituting the time-series images of an object to be examined, which are captured in time series, into category areas including an examined area and an abnormal candidate area, the examined area showing the object to be examined, the abnormal candidate area being possibly an abnormal area showing an abnormal site of the object to be examined; an optical flow calculator that calculates optical flows of the examined area and the abnormal candidate area from images constituting the time-series images; and an abnormal area detector that compares the optical flow of the examined area and the optical flow of the abnormal candidate area, and detects the abnormal candidate area as the abnormal area according to the result of the comparison.

14 Claims, 9 Drawing Sheets

IMAGE PROCESSING APPARATUS, IMAGE PROCESSING PROGRAM RECORDING MEDIUM, AND IMAGE PROCESSING METHOD

CROSS-REFERENCE TO RELATED APPLICATIONS

This application is a continuation of PCT international application Ser. No. PCT/JP2009/060186 filed on Jun. 3, 2009 which designates the United States, incorporated herein by reference, and which claims the benefit of priority from Japanese Patent Application No. 2008-147996, filed on Jun. 5, 2008, incorporated herein by reference.

BACKGROUND OF THE INVENTION

1. Field of the Invention

The present invention relates to an image processing apparatus that processes time-series images that are captured in time series, an image processing program recording medium, and an image processing method.

2. Description of the Related Art

In recent years, medical apparatuses as represented by capsule endoscopes that sequentially capture time-series in-vivo images of a lumen (digestive tract) while moving through the lumen have been developed, which are apparatuses that examine a moving object to be examined from time-series images of the object to be examined that are captured in time series. A capsule endoscope is swallowed and then conveyed through the lumen, for example, due to peristalsis. The capsule endoscope sequentially captures images at a predetermined imaging rate and transmits the images to an external receiving device, and it is eventually excreted to the outside of the body. The number of captured time-series images is roughly represented by the imaging rate (about 2 to 4 frames/sec)×time for which the capsule endoscope stays in the body (about 8 hours=8×60×60 sec), which amounts to more than a few tens of thousands. Doctors spend much time on checking a large number of time-series images, which are recorded in the external receiving device, using a diagnostic work station in order to identify a lesion; therefore, technologies for facilitating operations of doctors to check the images are strongly demanded.

For example, Japanese Laid-open Patent Publication No. 2007-175432 discloses a method of detecting a lesion, which is an abnormal site, from time-series images that are captured by a capsule endoscope. Specifically, images that are sampled at predetermined intervals from time-series images are each divided into rectangular areas. After the rectangular areas are projected in a predetermined feature space, such as an average color ratio space, the rectangular areas are clustered. The resulting clusters are classified into classes of mucosa, feces (contents), and bubbles using a classifier that is prepared beforehand based on teaching data. Thereafter, the sampled images are divided into sub-sets at predetermined chronological intervals, and the frequency of occurrence and a distribution of feature data of each of the classes in each subset are calculated from the result of the classification into the classes. According to such information, the rectangular areas of the images in the chronological interval represented by each sub-set are classified into the classes. By comparing the feature data of each rectangle area, which is classified as mucosa in the image as a result of the classification, with average feature data of all the rectangular areas, which are classified as mucosa in the image, a lesion is detected.

SUMMARY OF THE INVENTION

An image processing apparatus according to an aspect of the present invention includes: a category area dividing unit that divides each image constituting time-series images of an object to be examined, which are captured in time series, into category areas including an examined area and an abnormal candidate area, the examined area showing the object to be examined, the abnormal candidate area being possibly an abnormal area showing an abnormal site of the object to be examined; an optical flow calculator that calculates optical flows of the examined area and the abnormal candidate area from images constituting the time-series images; and an abnormal area detector that compares the optical flow of the examined area and the optical flow of the abnormal candidate area, and detects the abnormal candidate area as the abnormal area according to the result of the comparison.

An image processing program recording medium according to another aspect of the present invention stores thereon instructions that causes an image processing apparatus to perform: a category area dividing procedure that divides each image constituting time-series images of an object to be examined, which are captured in time series, into category areas including an examined area and an abnormal candidate area, the examined area showing the object to be examined, the abnormal candidate area being possibly an abnormal area showing an abnormal site of the object to be examined; an optical flow calculating procedure that calculates optical flows of the examined area and the abnormal candidate area from images constituting the time-series images; and an abnormal area detecting procedure that compares the optical flow of the examined area and the optical flow of the abnormal candidate area, and detects the abnormal candidate area as the abnormal area according to the result of the comparison.

An image processing method according to still another aspect of the present invention includes: a category area dividing step that divides each image constituting time-series images of an object to be examined, which are captured in time series, into category areas including an examined area and an abnormal candidate area, the examined area showing the object to be examined, the abnormal candidate area being possibly an abnormal area showing an abnormal site of the object to be examined; an optical flow calculating step that calculates optical flows of the examined area and the abnormal candidate area from images constituting the time-series images; and an abnormal area detecting step that compares the optical flow of the examined area and the optical flow of the abnormal candidate area, and detects the abnormal candidate area as the abnormal area according to the result of the comparison.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention will be described in detail below with reference to the drawings. Hereinafter, an image processing apparatus will be described that processes time-series images of the interior of a lumen as an object to be examined, which are captured in time series by a capsule endoscope, and that detects, as an abnormal site, a lesion on a mucosa area that is an example of an examined area. Note that time-series images that the image processing apparatus can process are not limited to time-series in-vivo images of a lumen. The present invention is applicable to detection of an abnormal site on an object to be examined from time-series images of a moving object to be examined, which are captured in time series.

Figure 1:
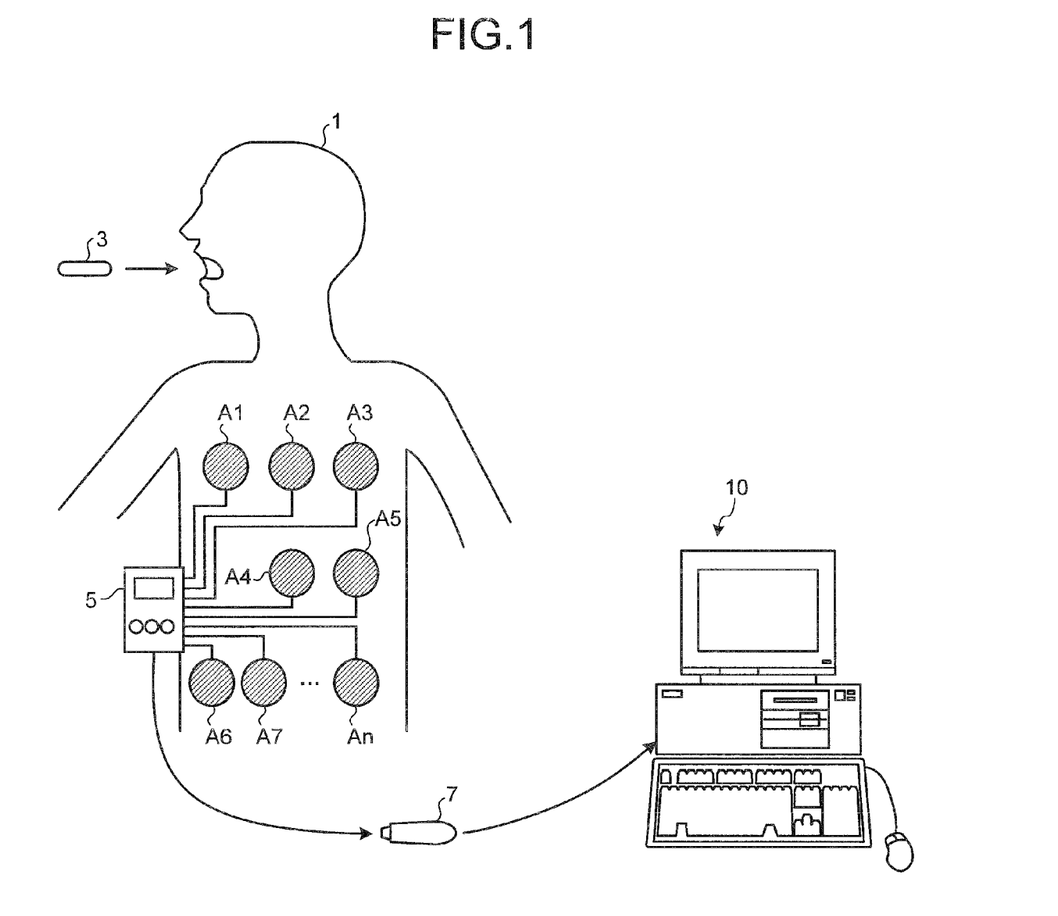
FIG. 1 is a schematic diagram of an entire configuration of an image processing system that includes an image processing apparatus.

FIG. 1 is a schematic diagram of an entire configuration of an image processing system that includes an image processing apparatus according to an embodiment. As illustrated in FIG. 1, the image processing system includes a capsule endoscope 3 that captures in-vivo images of a subject 1 (lumen in-vivo images); a receiving device 5 that receives lumen in-vivo images that are transmitted by radio from the capsule endoscope 3; and an image processing apparatus 10 that processes the lumen in-vivo images, which are captured by the capsule endoscope 3, using the lumen in-vivo images that are received by the receiving device 5 and then displays the processed lumen in-vivo images. For example, a recording medium 7 that is portable (portable recording medium) is used for transmission and reception of image data between the receiving device 5 and the image processing apparatus 10.

The capsule endoscope 3 has an imaging function and a radio function. The capsule endoscope 3 is swallowed by the subject 1 and is introduced into the subject 1. The capsule endoscope 3 sequentially captures lumen in-vivo images while moving through the lumen. The capsule endoscope 3 transmits the lumen in-vivo images by radio to the outside of the body.

The receiving device 5 includes receiving antennas A1 to An that are discretely arranged on the body surface in positions corresponding to a path along which the capsule endoscope 3 travels in the subject 1. The receiving device 5 receives image data that is transmitted by radio from the capsule endoscope 3 via the receiving antennas A1 to An. The receiving device 5 is configured such that the portable recording medium 7 can be attached and detached, and the receiving device 5 saves the received image data in the portable recording medium 7 each time image data is received. Thus, the receiving device 5 stores lumen in-vivo images of the subject 1, which are captured by the capsule endoscope 3, in the portable recording medium 7 in chronological order as time-series images.

Figure 2:
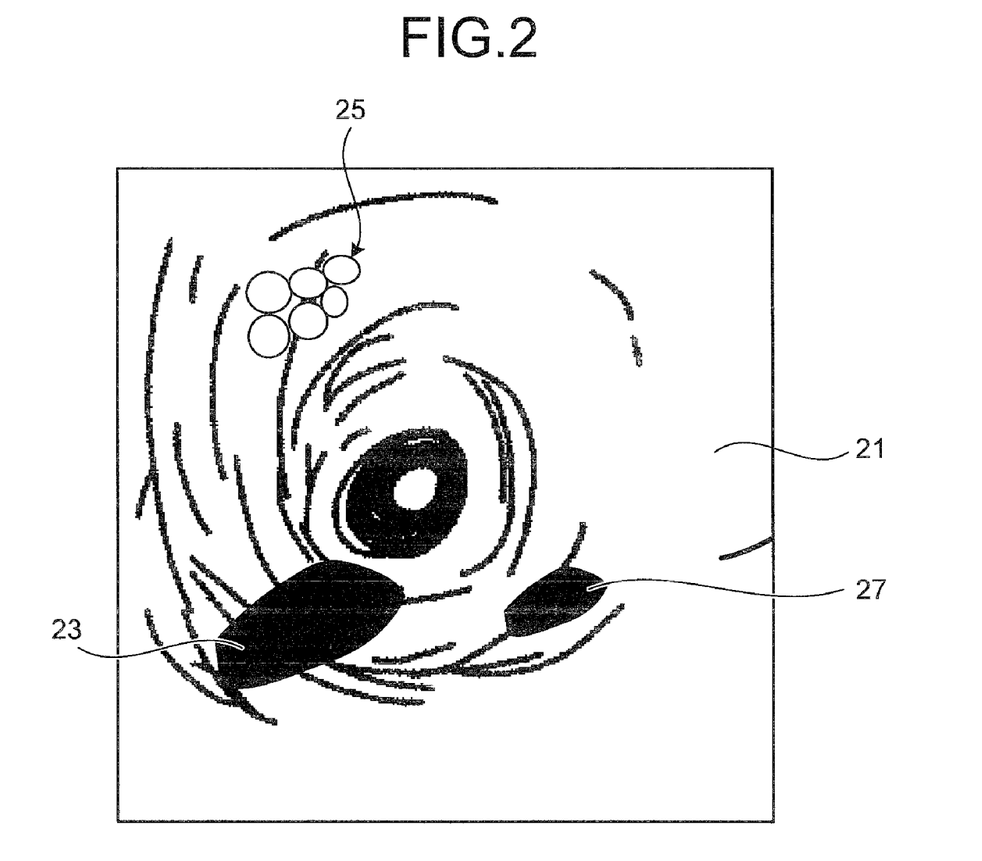
FIG. 2 is a view of an example of a lumen in-vivo image.

The image processing apparatus 10 is used by doctors to examine and diagnose lumen in-vivo images that are captured by the capsule endoscope 3. The image processing apparatus 10 is realized using a general-purpose computer, such as a work station or a personal computer. The image processing apparatus 10 is configured such that the portable recording medium 7 can be attached and detached. The image processing apparatus 10 processes each lumen-in-vivo image constituting time-series images, which are saved in the portable recording medium 7, and sequentially displays the processed lumen-in-vivo images on a display, such as an LCD or an ELD, in time series. FIG. 2 is a view of an example of a lumen in-vivo image that is captured by the capsule endoscope 3 and is processed by the image processing apparatus 10. The lumen in-vivo image shows a mucosa 21, contents 23 and bubbles 25 that float in the lumen and, occasionally, shows a crucial part, such as a lesion 27. Lumen in-vivo images that are captured by the capsule endoscope 3 are color images each having a pixel level (pixel value) corresponding to each color component of R (red), G (green), or B (blue) at each pixel position.

Figure 3:
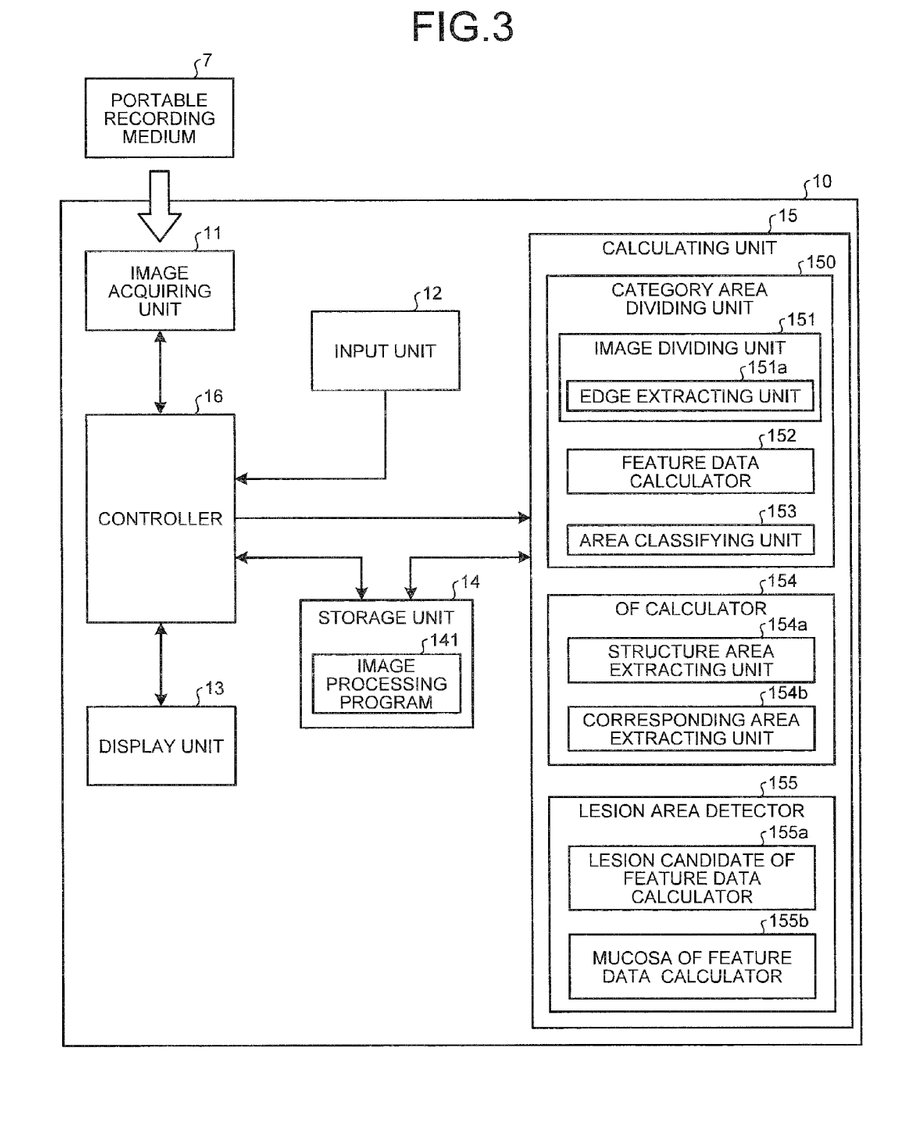
FIG. 3 is a block diagram illustrating a functional configuration of the image processing apparatus.

FIG. 3 is a block diagram illustrating a functional configuration of the image processing apparatus 10. In this embodiment, the image processing apparatus 10 includes an image acquiring unit 11, an input unit 12, a display unit 13, a storage unit 14, a calculating unit 15, and a controller 16 that controls each unit of the apparatus.

The image acquiring unit 11 captures lumen in-vivo images constituting time-series images that are captured by the capsule endoscope 3 and are saved by the receiving device 5 in the portable recording medium 7. For example, the portable recording medium 7 is detachably attached to the image acquiring unit 11, and the image acquiring unit 11 acquires the image data of the lumen in-vivo images stored in the attached portable recording medium 7 by reading the lumen in-vivo images. The image acquiring unit 11 is realized using, for example, a reading and writing device corresponding to the type of the portable recording medium 7. Acquisition of time-series lumen in-vivo images that are captured by the capsule endoscope 3 are not limited to the configuration using the portable recording medium 7. For example, a configuration may be employed using, instead of the image acquiring unit 11, a hard disk and in which time-series lumen in-vivo images that are captured by the capsule endoscope 3 are saved beforehand. Alternatively, a configuration may be employed in which an additional server is arranged instead of the portable recording medium 7 and time-series lumen in-vivo images are saved in the server beforehand. In such a case, the image acquiring unit is configured as a communication device for establishing connection with the server. Connection is established with the server via the image acquiring unit and the time-series in-vivo images are acquired from the server.

The input unit 12 is realized by, for example, a keyboard, a mouse, a touch panel, and various switches. The input unit 12 outputs operation signals corresponding to operational inputs to the controller 16. The display unit 13 is realized using a display device, such as an LCD or an ELD. Under control of the controller 16, the display unit 13 displays various screens including the screen on which time-series lumen in-vivo images are displayed.

The storage unit 14 is realized using various IC memories, such as rewritable flash memories, including ROMs and RAMs; a hard disk that is incorporated or connected via a data communication terminal; an information recording medium, such as a CD-ROM; and a reading device for the information recording medium. The storage unit 14 stores programs for operating the image processing apparatus 10 and for performing various functions of the image processing apparatus 10 and stores data that is used during execution of the programs. The storage unit 14 also stores an image processing program 141 for detecting a lesion, which is an abnormal site, from lumen in-vivo images constituting time-series images.

The calculating unit 15 is realized using hardware, such as a CPU. The calculating unit 15 sequentially processes time-series lumen in-vivo images that are acquired by the image acquiring unit 11 and performs various arithmetic processes to perform classification on each in-vivo image into category areas. The calculating unit 15 includes a category area dividing unit 150; an optical flow (hereinafter, "OF") calculator 154, and a lesion area detector 155 that corresponds to an abnormal area detector. The category area dividing unit 150 divides each image constituting the time-series images (lumen in-vivo images), which are captured by the capsule endoscope 3 moving through the lumen, into predetermined category areas that include a mucosa area and a lesion candidate area. The category area dividing unit 150 includes an image dividing unit 151, a feature data calculator 152, and an area classifying unit 153. The image dividing unit 151 serves as a function unit that divides an image into plural areas. The image dividing unit 151 includes an edge extracting unit 151a that extracts edges in an image. The feature data calculator 152 calculates feature data of each divided area. The area classifying unit 153 classifies the divided areas into predetermined categories according to the feature data. The OF calculator 154 calculates optical flows of a mucosa area and a lesion candidate area. The OF calculator 154 includes a structure area extracting unit 154a and a corresponding area extracting unit 154b. The structure area extracting unit 154a extracts a structure area from each image constituting the time-series images. The corresponding area extracting unit 154b extracts a corresponding area, which corresponds to the structure area, from another image that is captured at a time different from that of the image from which the structure area is extracted. The lesion area detector 155 detects a lesion area by comparing optical flows of a mucosa area and optical flows of a lesion candidate area. The lesion area detector 155 includes a lesion candidate OF feature data calculator 155a that serves as an abnormal candidate optical flow feature data calculator and includes a mucosa OF feature data calculator 155b that serves as an examined optical flow feature data calculator. The lesion candidate OF feature data calculator 155a calculates feature data of optical flows of a lesion candidate area. The mucosa OF feature data calculator 155b calculates feature data of optical flows of a mucosa area that is positioned around a lesion candidate area.

The controller 16 is realized using hardware, such as a CPU. The controller 16 generally controls all the operations of the image processing apparatus 10 by transferring instructions and data to each unit forming the image processing apparatus 10 in accordance with image data, which is input from the image acquiring unit 11, operation signals, which are input from the input unit 12, and the programs and data, which are stored in the storage unit 14.

Figure 4:
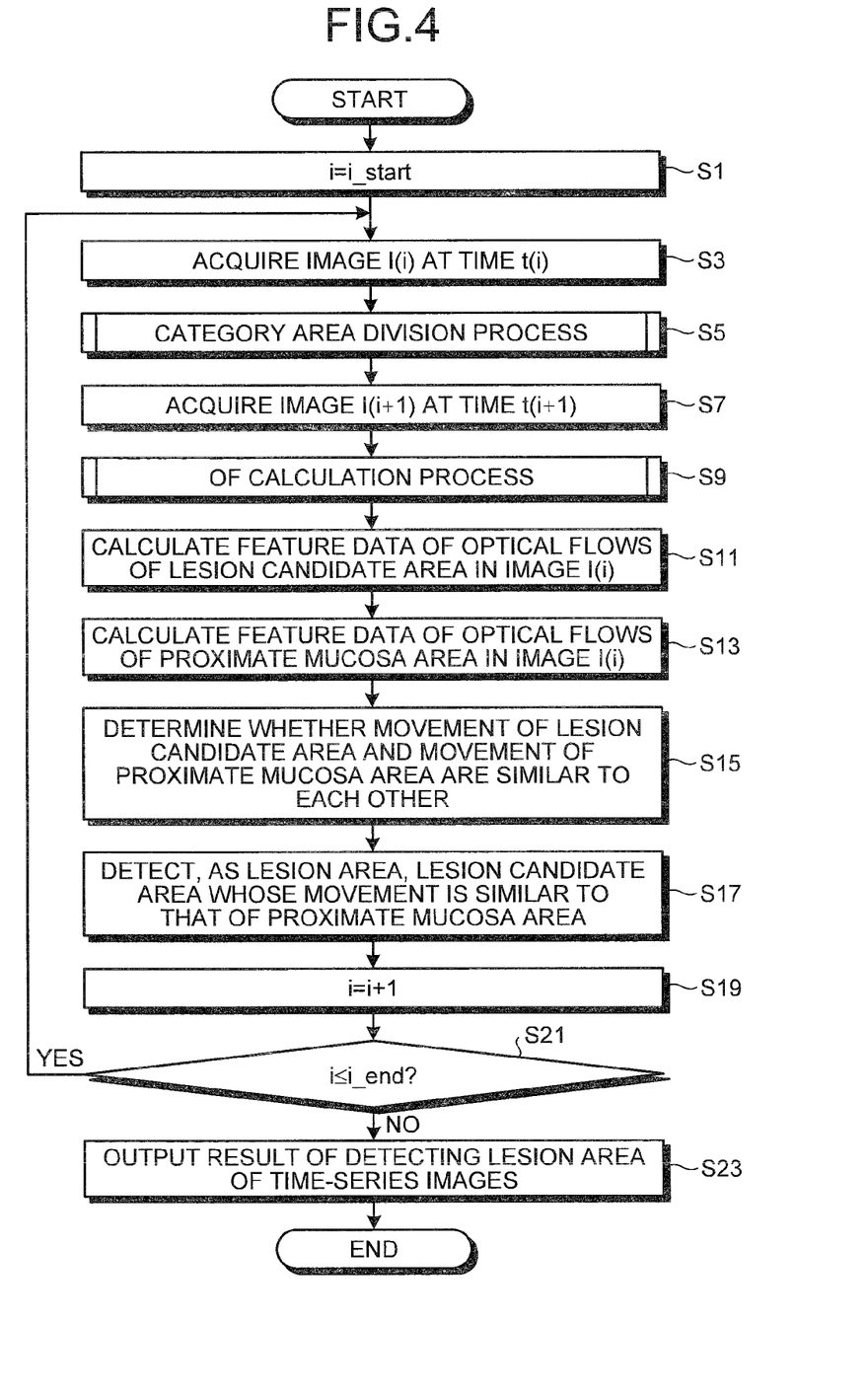
FIG. 4 is a flowchart of a whole process procedure that is performed by the image processing apparatus.

FIG. 4 is an overall flowchart of a process procedure that is performed by the image processing apparatus 10. The process described here is performed by the calculating unit 15 by executing the image processing program 141 stored in the storage unit 14. FIG. 4 illustrates the flow of processing images of I(i_start) to I(i_end) in chronological order of i_start to i_end, which are lumen in-vivo images constituting time-series images.

As illustrated in FIG. 4, first, the calculating unit 15 sets a reference symbol i, which represents a chronological order, as i_start (step S1) and acquires an image I(i) at a chronological order i (step S3).

Figure 5:
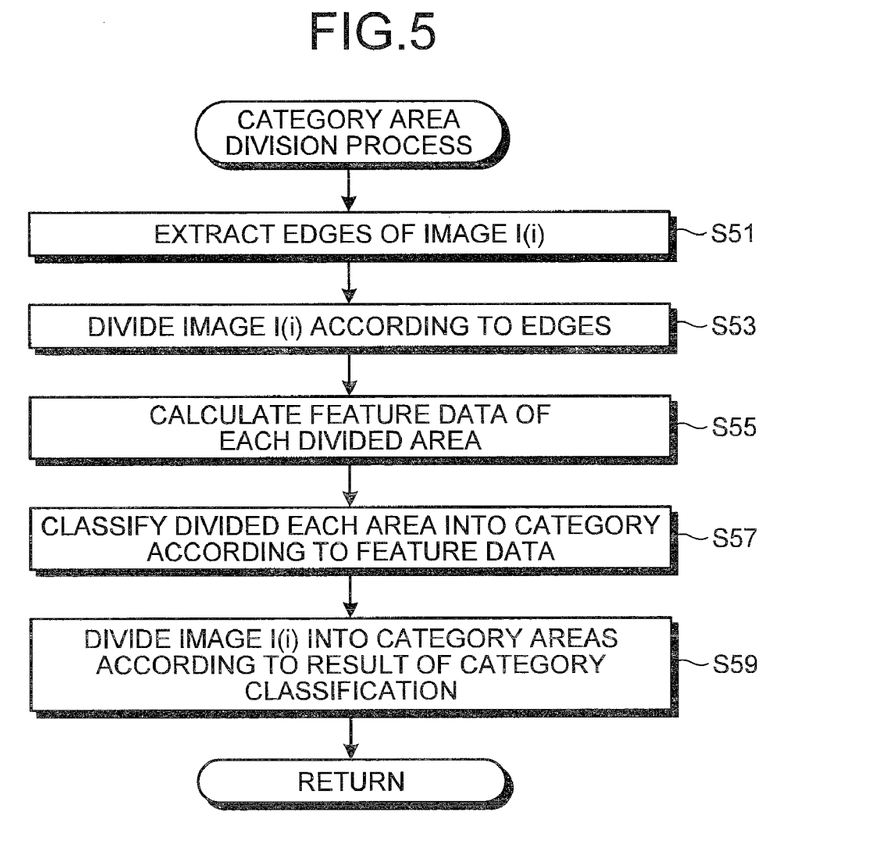
FIG. 5 is a flowchart of a detailed process procedure of a category area division process.

The category area dividing unit 150 then performs a category area division process to divide the image I(i) into predetermined categories (step S5). FIG. 5 is a flowchart of a detailed process procedure of the category area division process.

In the category area division process, first, the edge extracting unit 151a extracts edges of the image I(i) (step S51). In the procedure, first, a G component image consisting of G components of the image I(i) is generated. The G components are used because their absorption wavelength band is close to that of the hemoglobin in blood and their sensitivity and resolution are high, thereby satisfactorily representing structure information of the lumen in-vivo image. Alternatively, other components may be used or values may be used of luminance, color difference (YCbCr conversion), hue, saturation, brightness (HSI conversion), and color ratio that are secondarily calculated from the color components of the image I(i) by a well-known conversion process. Space filtering is performed on the G component image using a well-known primary differential filter (a Prewitt filter or a Sobel filter) or a secondary differential filter (a Laplacian filter or an LoG (Laplacian of Gaussian) filter) in order to extract edges (see, CG-ARTS Association, Digital image processing, p. 114, Edge detection).

The image dividing unit 151 divides the image I(i) according to the edges (step S53). The method disclosed in International Publication Pamphlet No. WO2006/080239 may be used for the method of dividing an image according to the edges. The procedure will be briefly described. First, a smoothing process is performed on the image, from which edges have been extracted, in order to remove noise as required. Thereafter, gradient directions of pixel values of the respective pixels of the image, from which edges have been extracted and on which the smoothing process has been performed, are obtained. The gradient direction is such that the difference in the pixel values between a pixel and neighboring pixels are a minimum (negative value is the maximum). An extreme value pixel to which each pixel reaches along the gradient direction is obtained, and the image is divided such that pixels that reach an adjacent extreme pixel are in the same area.

A watershed algorithm may be used as an alternative division method (see Luc Vincent and Pierre Soille. Watersheds in digital spaces: An efficient algorithm based on immersion simulations. Transaction Pattern Analysis and Machine Intelligence, Vol. 13, No. 6, pp. 583-598, June, 1991). The watershed algorithm is a method in which an image is divided such that, when water is filled in the geography, assuming that pixel value information of the image is the altitude, boundaries are formed in the water that is kept in different depressions. As described above, an image can be divided according to edges by performing appropriate smoothing on the image from which edges have been extracted and then by executing a watershed algorithm.

The method of dividing an image according to edges is described above. By dividing the image according to the edges as described above, image division is performed in which the boundaries of an object to be imaged are reflected. This improves accuracy in the calculation of optical flows, which will be described below. Alternatively, a method of dividing an image into rectangular areas in a predetermined size without performing edge detection may be employed. In this case, the process time can be shortened compared with the case in which an image is divided according to edges.

The feature data calculator 152 then calculates feature data of each divided area (step S55). Feature data may be statistical amounts such as an average, skewness, kurtosis and a histogram, frequency features, texture information such as a simultaneous normal matrix of R, G, and B components of pixel values in an area (see CG-ARTS Association: Digital image processing, p. 192, Area feature data) or statistical amounts and texture information that are secondarily calculated from the R, G, and B components, such as luminance, color difference, hue, saturation, brightness, or color ratio. By collectively calculating such feature data of each divided area instead of each pixel, the feature data containing the relation with neighboring pixels can be obtained.

When using image data that is coded and compressed by performing discrete cosine transform (DCT) on each compartment of imaged data, such as a JPEG data, the image is divided according to the compartments used for coding and compression without the above-described edge extraction, and a DCT coefficient that is obtained for each compartment when decompressing the data or a value that is calculated secondarily from the DCT coefficient may be used as the feature data.

The area classifying unit 153 classifies each divided area into a category according to the feature data (step S57). In this embodiment, each divided area is classified into any one of categories of mucosa, lesion candidate, or others. There are various classification methods. In this example, teaching data is prepared beforehand, in which feature data and a correct category are paired for each divided area, and event probability of each category and a probability density function of each category are obtained beforehand. With reference to the teaching data, the event probability, and the probability density function, the divided areas are classified according to their feature data.

First, event probability Pc(i) (i=1 to NC) of each category is obtained, using the number of pieces of each category data of the prepared teaching data, according to the following Equation (1), where NC denotes the number of categories and ND(i) denotes the number of pieces of data in a category (i).

$$Pc(i) = \frac{ND(i)}{\sum_{j=1}^{NC} ND(j)} \quad (1)$$

Thereafter, a feature vector $Fn=(fn\_1, fn\_2, \ldots, fn\_k)^t$ is calculated where fn_i is the value of the ith feature data of the nth teaching data and k is the number of dimensions of the feature data. Using the obtained feature vector Fn, an average vector μ and a variance-covariance matrix Z are obtained for each category according to the following Equation (2).

$$\mu = \frac{1}{ND} \sum_{n=1}^{ND} Fn, \quad (2)$$

$$Z = \frac{1}{ND} \sum_{n=1}^{ND} (Fn - \mu)(Fn - \mu)^t$$

A coefficient of a probability density function P(x) represented in the following Equation (3) is then calculated for each category.

$$P(x) = \frac{1}{(2\pi)^{K/2} \times |Z|^{1/2}} \exp\left\{(x-\mu)^t \times -\frac{1}{2} Z^{-1} \times (x-\mu)\right\} \quad (3)$$

Note that |Z| is a determinant of Z, $Z^{-1}$ is an inverse matrix of Z, and x is a feature vector to be determined. The event probability Pc(i) of each category obtained using the teaching data and the values of coefficients of the probability density function P(x)(i) of each category are stored in the storage unit 14, where the values of the coefficients of the probability function P(x)(i) are $$\frac{1}{(2\pi)^{K/2} \times |Z|^{1/2}}, \mu, \text{ and } -\frac{1}{2} Z^{-1}.$$

Probability of attribution of a divided area to be classified into each category is calculated by calculating Pc(i)×P(x)(i) (i=1 to NC) using each stored value and the stored feature vector x of the divide area to be classified. The divided area is classified into the category of the highest attribute probability. After all the divided areas are classified, the process goes to step S59.

Figure 6:
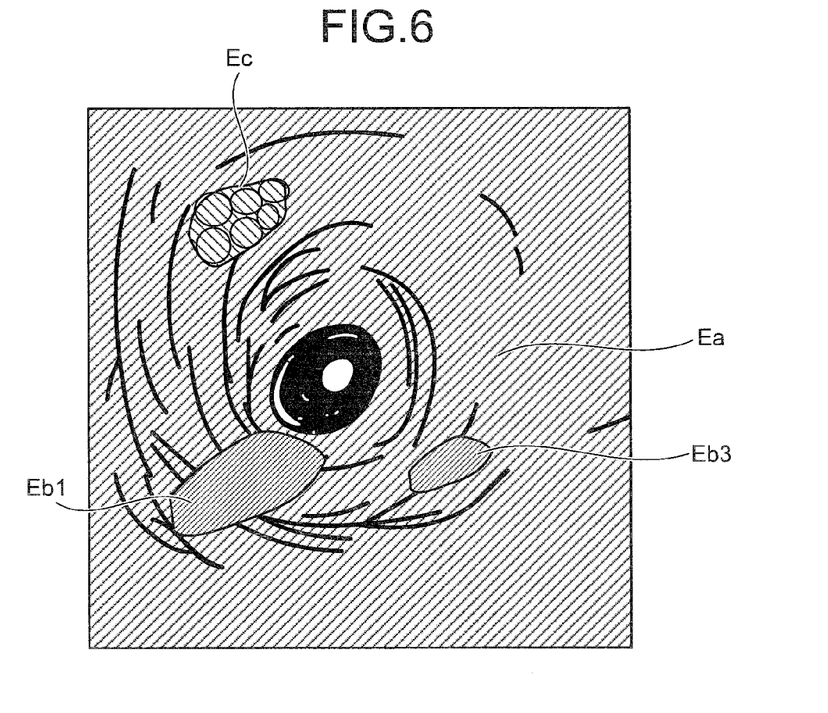
FIG. 6 is a view of an example of the result of dividing the lumen in-vivo image in FIG. 2 into category areas.

Specifically, at step S59, the category area dividing unit 150 divides the image I(i) into category areas according to the result of the category classification. This can be done by imaging the result of the classification of each divided area. FIG. 6 represents an example of a result of dividing the lumen in-vivo image in FIG. 2 into category areas. In the example illustrated in FIG. 6, the image is classified into a mucosa area Ea, lesion candidate areas Eb1 and Eb3, and other area Ec.

The example is described above in which the image I(i) is divided into category areas by dividing the image and classifying the divided areas into categories. However, the category division is not limited to this. For example, without dividing the image, feature data of the respective pixels may be calculated and the pixels may be classified into categories according to the feature data so that the image I(i) is divided into categories. When the image I(i) has been divided into category areas, the process returns to step S5 in FIG. 4 and goes to step S7.

Figure 7:
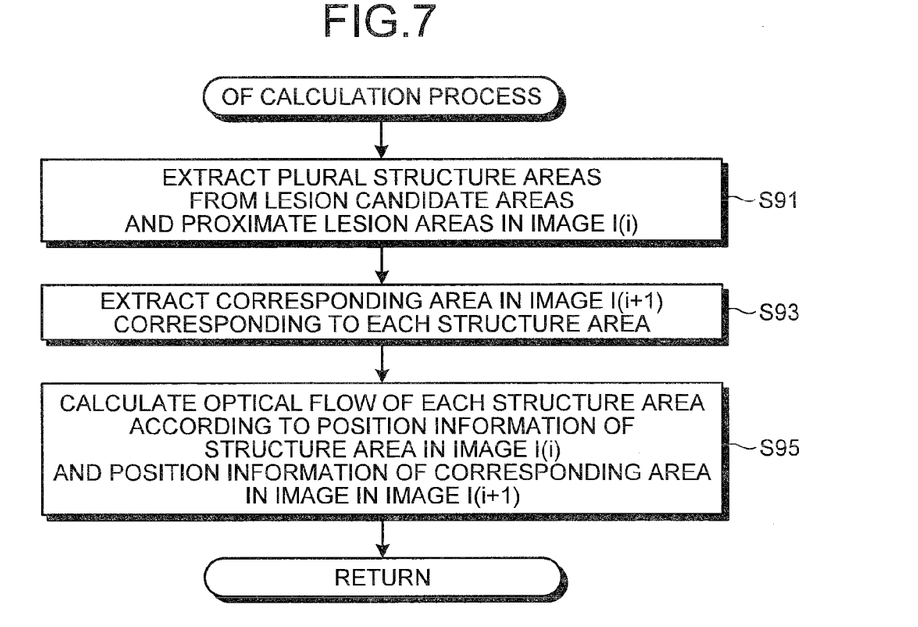
FIG. 7 is a flowchart of a detailed process procedure of an OF calculation process.

Specifically, at step S7, the calculating unit 15 acquires an image I(i+1) at a chronological order i+1 that is subsequent to the image I(i). The OF calculator 154 performs an OF calculation process in order to calculate optical flows of the lesion candidate areas and the mucosa area proximate to the lesion candidate area (hereinafter, "proximate mucosa area") in the image I(i) (step S9). The optical flow is obtained by associating the same object (object position) between two images that are captured at different times and by representing the displacement between the two images as vector data. There are various methods for calculating an optical flow. In this embodiment, a case is described in which an optical flow is calculated using block matching. FIG. 7 is a flowchart of a detailed process procedure of the OF calculation process.

In the OF calculation process, first, the structure area extracting unit 154a extracts plural structure areas from each of the lesion candidate area and the proximate mucosa area of the lesion candidate area in the image I(i) (step S91). The structure areas are areas that can be associated between images at different times and are areas that show structures that characterize local sites in the mucosa area and the lesion candidate areas (hereinafter, "feature structure"). Normally, gathers, wrinkles, and blood vessels that can be seen through the surface are different in shape in each portion, thereby serving as feature structures.

In the procedure of extracting structure areas, first, rectangular areas in a predetermined size are set in the lesion candidate area and the proximate mucosa area of the lesion candidate area in the image I(i). By referring to the result of the category area division in a rectangular area, a determination is made of whether the rectangular area is the mucosa area or the lesion candidate area. By making a determination of whether there is the lesion candidate area in a neighboring area in a predetermined area around a rectangular area that is set as the mucosa area, it is determined whether the rectangular area is the proximate mucosa area positioned proximate to the lesion candidate area.

Subsequently, a distribution range is obtained from maximum values and minimum values of the pixel values of the G components in the rectangular area and the distribution range is stored in the storage unit 14. The G components are used because, as described above, their absorption wavelength band is close to that of the hemoglobin in blood and their sensitivity and resolution are high, thereby satisfactorily representing structure information of the lumen in-vivo image. Alternatively, other components may be used or values may be used of luminance, color difference (YCbCr conversion), hue, saturation, brightness (HSI conversion), and color ratio that are secondarily calculated from the color components of the image I(i) by a well-known conversion process. When the distribution range of the pixel values is small, the pixel values in the rectangular area are uniform, indicating low probability that a feature structure is shown in the rectangular area. In contrast, when the distribution range of the pixel values is large, there is high probability that a feature structure is shown in the rectangular area. Note that, when calculating a distribution range of pixel values, it is not necessary to use all the pixels in a rectangular area. For example, the distribution range of the pixel values may be calculated using a unidirectional elongated row of pixels or using two rows of pixels that are bidirectional and intersect with each other. In addition to the distribution range, for example, other indices representing the expanse of the distribution of the pixel values, such as dispersion or standard deviation, may be obtained.

The positions of the rectangular areas are changed and set such that the lesion candidate area and the proximate mucosa area of the lesion candidate area are scanned. The process moves to the calculation of distribution ranges of pixel values in the newly-set rectangular areas. A predetermined number of rectangular areas are extracted, from the finally-set rectangular areas, in descending order of the sizes of the stored distribution ranges of pixels. The amount in which rectangular areas overlap is set to be equal to or less than a predetermined value.

Figure 8:
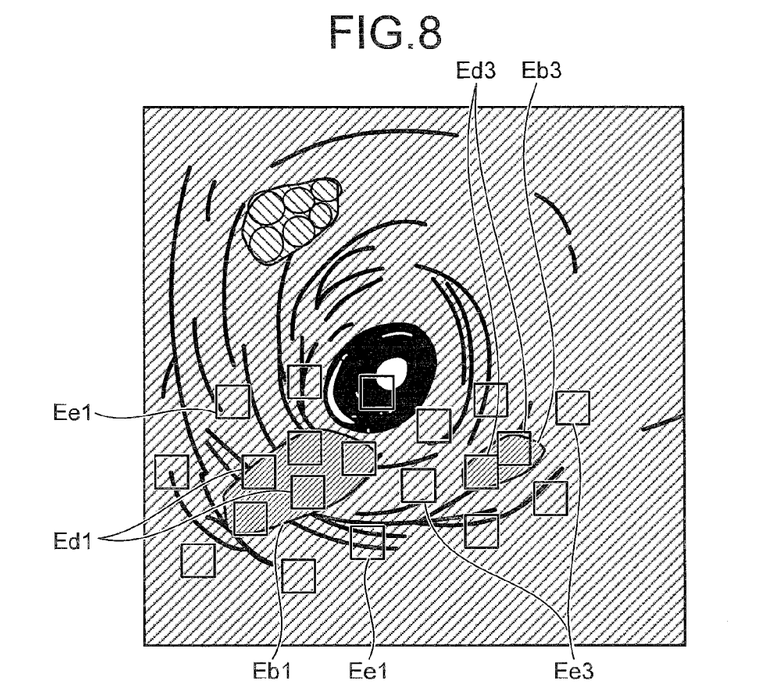
FIG. 8 is a view of an example of the result of extracting structure areas based on the result of the category area division illustrated in FIG. 6.

FIG. 8 is a view of an example of a result of extracting structure areas from a lesion candidate area and a proximate mucosa area based on the result of the category area division illustrated in FIG. 6. As illustrated in FIG. 8, structure areas Ed1 are extracted in the lesion candidate area Eb1 and structure areas Ed3 are extracted in the lesion candidate area Eb3. Furthermore, structure areas Ee1 are extracted in the proximate mucosa, which is positioned proximate to the lesion candidate area Eb1, and structure areas Ee3 are extracted in the proximate mucosa, which is positioned proximate to the lesion candidate area Eb3.

The method of extracting appropriate plural rectangular areas as structure areas while scanning rectangular areas of a predetermined size is described above. However, the method of extracting structure areas is not limited to this. For example, without scanning rectangular areas, an image may be divided beforehand into rectangular areas of a predetermined size. Thereafter, a determination of whether a rectangular area is a lesion candidate area or a proximate mucosa area may be made on each of the rectangular areas, a distribution range of pixel values may be calculated for each area determined to be a lesion candidate area or a proximate mucosa area, and a predetermined number of rectangular areas may be extracted as structure areas in descending order of the sizes of the stored distribution areas of pixels. Alternatively, the above-described processes may be performed not on rectangular areas of the predetermined size but on the divided areas that are divided according to the edges by the image dividing unit 151. In this case, the shape of the areas is not limited to a rectangle. Employing this method shortens the process time compared with the case in which structure areas are extracted during scanning.

Subsequently, as illustrated in FIG. 7, the corresponding area extracting unit 154b extracts an area in the image I(i+1), which is an area corresponding to each structure area (step S93). In the procedure, first, each structure area is set in a template and a well-known template matching process is performed on the image I(i+1) (see, CG-ARTS Association, Digital image processing, p. 202, Template matching). A search area of the matching may be set in consideration of the amount of variations between time-series images, centering on the center coordinates (xi, yi) of each template. To increase the process speed, a coarse-to-fine search method or a sequential similarity detection method may be used (see, CG ARTS Association, Digital image processing, p. 206, High speed search method). As a result, the coordinates (xi', yi') of the most similar area in the image I(i+1) and the similarity are obtained for each structure area. With respect to a template with a low degree of similarity in matching, there is low probability that the same object is associated; therefore, the following optical flow calculation is not performed.

Figure 9:
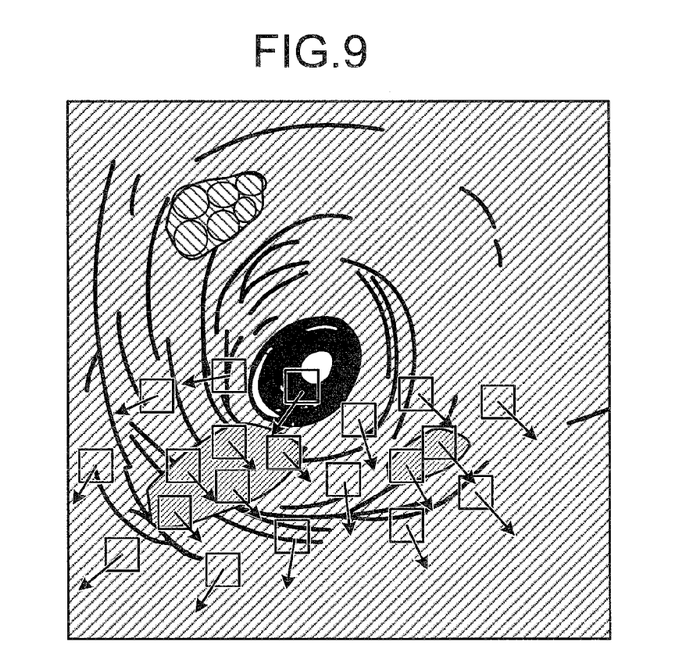
FIG. 9 is a view schematically showing optical flows that are calculated for the structure areas in FIG. 8, respectively.

Subsequently, the OF calculator 154 calculates an optical flow of each structure area using the position information of the structure area in the image I(i) and the position information of the corresponding area in the image I(i+1) (step S95). An optical flow of each structure area can be obtained by obtaining a vector from the center coordinates of each structure area in the image I(i) to the center coordinates of the corresponding area in the image I(i+1) corresponding to the structure area. FIG. 9 is a view schematically representing the calculated optical flows of the structure areas, illustrated in FIG. 8, using arrows. Once the optical flows of the respective structure areas are calculated, the process returns to step S9 in FIG. 4 and moves to step S11.

At step S11, the lesion candidate OF feature data calculator 155a calculates feature data of the optical flows of a lesion candidate area in the image I(i). For example, as feature data of optical flows, an OF distribution is calculated that represents a distribution of end points of the optical flows with the start points being joined together, which are optical flows each calculated for a structure area in the lesion candidate area in the image I(i).

Figure 10:
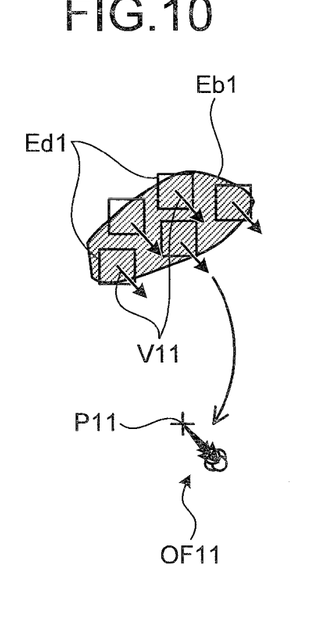
FIG. 10 is a view of an example of an OF distribution that is calculated for a lesion candidate area.
Figure 11:
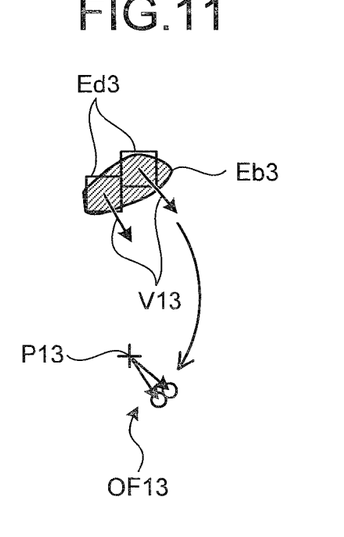
FIG. 11 is a view of another example of an OF distribution that is calculated for a lesion candidate area.

FIG. 10 is a view of an example of an OF distribution OF11 that is calculated for the lesion candidate area Eb1 in FIG. 6. FIG. 11 is a view representing an example of an OF distribution OF13 that is calculated for the lesion candidate area Eb3 in FIG. 6. As illustrated in FIG. 10, the OF distribution OF11 of the lesion candidate area Eb1, i.e., the distribution of the end points of the optical flows V11 with the start points being joined together at one point P11, which are optical flows calculated for the respective structure areas Ed1 in the lesion candidate area Eb1, concentrate on the lower right in FIG. 10. Similarly, as illustrated in FIG. 11, the OF distribution OF13 of the lesion candidate area Eb3, i.e., the distribution of the end points of the optical flows V13 with the start points being joined together at one point P13, which are optical flows calculated for the respective structure areas Ed3 in the lesion candidate area Eb3, concentrate on the lower right in FIG. 10.

The process for dividing a lesion candidate area in consideration of connectivity between pixels can be realized using a well-known labeling process. The process is not limited to the OF distribution described in this example. A direction that is obtained by adding vectors of optical flows or an average value of the magnitudes of optical flows may be calculated as the feature data of optical flows.

Subsequently, as illustrated in FIG. 4, the mucosa OF feature data calculator 155b calculates the feature data of optical flows of a mucosa area that is positioned proximate to a lesion candidate area (hereinafter, "OF feature data") (step S13). For example, the mucosa OF feature data calculator 155b calculates an OF distribution of the proximate mucosa area using a procedure similar to that for calculating an OF feature data by the lesion candidate OF feature data calculator 155a.

Figure 12:
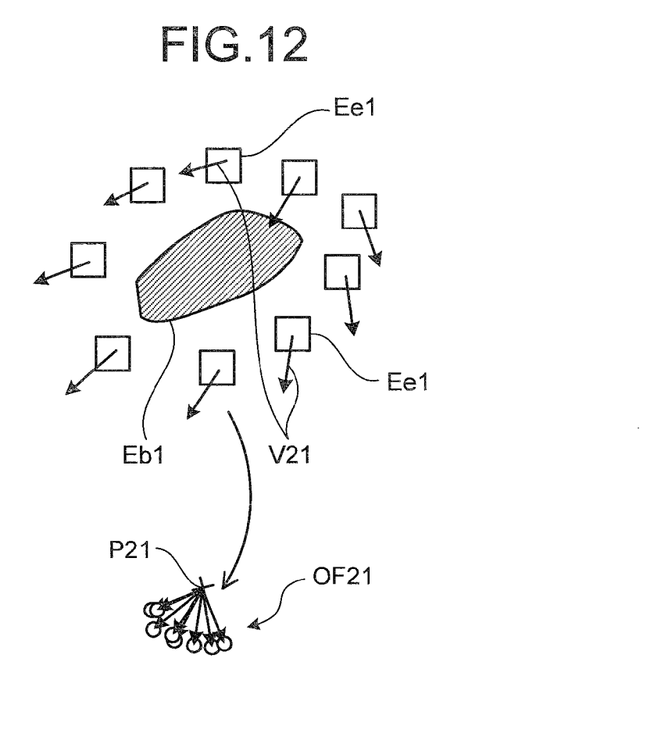
FIG. 12 is a view of an example of an OF distribution that is calculated for a proximate mucosa area of the lesion candidate area.
Figure 13:
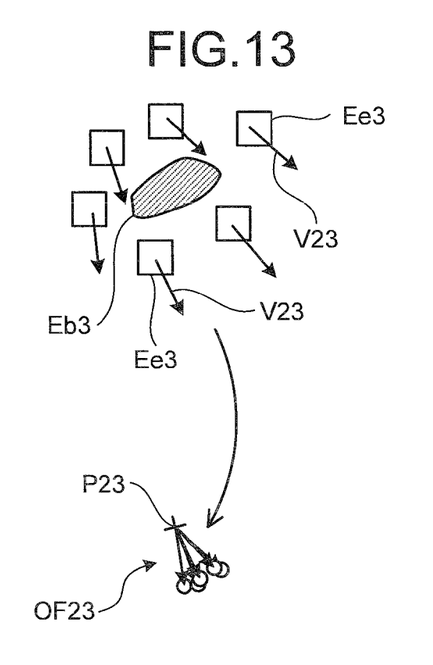
FIG. 13 is a view of another example of an OF distribution that is calculated for a proximate mucosa area of the lesion candidate area.

FIG. 12 is a view of an example of an OF distribution OF21 that is calculated for a proximate mucosa area of the lesion candidate area Eb1 in FIG. 6. FIG. 13 is a diagram of an example of an OF distribution OF 23 that is calculated for a proximate mucosa area of the lesion candidate area Eb3 in FIG. 6. As illustrated in FIG. 12, an OF distribution OF21 of a proximate mucosa area of the lesion candidate area Eb1, i.e., the distribution of the end points of optical flows V21 with the start points being joined together at one point P21, which are optical flows calculated for the respective structure areas Ee1 in the proximate mucosa area of the lesion candidate area Eb1, concentrate on the lower left in FIG. 12. In contrast, as illustrated in FIG. 13, an OF distribution OF23 of a proximate mucosa area of the lesion candidate area Eb3, i.e., the distribution of the end points of optical flows V23 with the start points being joined together at one point P23, which are optical flows calculated for the structure areas Ee3 in the proximate mucosa area of the lesion candidate area Eb3, concentrate on the lower right in FIG. 13.

Figure 14:
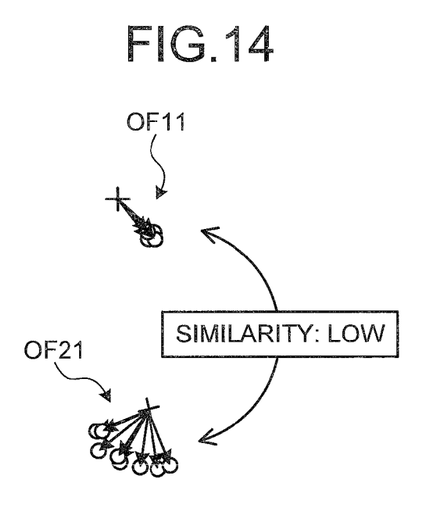
FIG. 14 is a view in which the OF distribution of the lesion candidate area illustrated in FIG. 10 and the OF distribution of the proximate mucosa area of the lesion candidate area illustrated in FIG. 12 are compared with each other.
Figure 15:
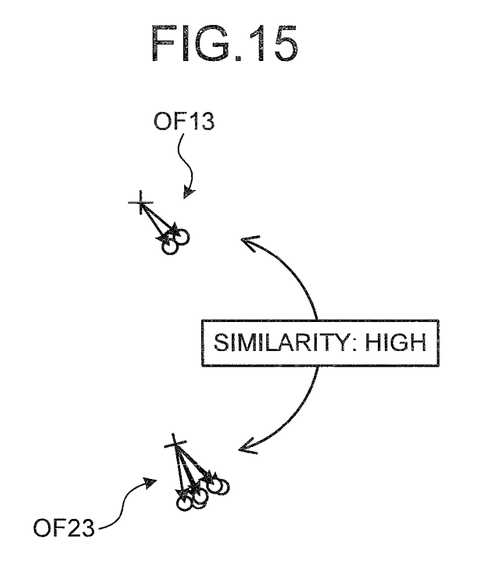
FIG. 15 is a view in which the OF distribution of the lesion candidate area illustrated in FIG. 11 and the OF distribution of the proximate mucosa area of the lesion candidate area illustrated in FIG. 13 are compared with each other.

Subsequently, as illustrated in FIG. 4, the lesion area detector 155 determines whether the movement of the lesion candidate area and the movement of the proximate mucosa area are similar to each other by obtaining a difference between the OF feature data obtained for the optical flows of the lesion candidate area and the OF feature data obtained for the optical flows of the proximate mucosa area and then performing a threshold process (step S15). FIG. 14 is a diagram in which the OF distribution OF11 of the lesion candidate area Eb1 illustrated in FIG. 10 and the OF distribution OF21 of the proximate mucosa area of the lesion candidate area Eb1 illustrated in FIG. 12 are represented in comparison with each other. FIG. 15 is a diagram in which the OF distribution OF13 of the lesion candidate area Eb3 illustrated in FIG. 11 and the OF distribution OF23 of the proximate mucosa area of the lesion candidate area Eb3 illustrated in FIG. 13 are represented in comparison with each other. As illustrated in FIG. 14, the difference between the OF feature data (OF distribution) of the lesion candidate area Eb1 and the proximate mucosa area of the lesion candidate area Eb1 is large, and thus it is determined that the similarity between the OF feature data is low. In contrast, as illustrated in FIG. 15, the difference between the OF feature data (OF distribution) of the lesion candidate area Eb3 and the proximate mucosa area of the lesion candidate area Eb3 is small, and thus it is determined that the similarity between the OF feature data is high.

Specifically, in the determination procedure, the distance between each point constituting the OF distribution of the lesion candidate area (the end point of each optical flow) and each point constituting the OF distribution of the proximate mucosa area is calculated as a difference between the feature data. The feature data may be a total of distances between every point and every other point, the distance between points most distant from each other, or the distance between points most close to each other. When the calculated value is equal to or smaller than a predetermined threshold, it is determined that the similarity is high. This process is performed on each lesion candidate area.

As illustrated in FIG. 4, the lesion area detector 155 detects, as a lesion area, a lesion candidate area whose movement is similar to that of the proximate mucosa area (step S17). For example, in the example illustrated in FIG. 6, while the lesion candidate area Eb 3 is detected as a lesion area, the lesion candidate area Eb1 is not detected as a lesion area.

Thereafter, the calculating unit 15 makes a setting of i=i+1, the reference number i representing the chronological order of a lumen in-vivo image to be processed (step S19), and determines whether there is the next lumen in-vivo image to be processed. When i≦i_end (YES at step S21), the image is regarded as the next lumen in-vivo image to be processed and steps S3 to S21 are performed. When the result of the determination at step S21 is NO, the calculating unit 15 outputs the result of the lesion detection on the time-series images (step S23), and the process of the image processing apparatus 10 ends. For example, the calculating unit 15 outputs and displays the result of the lesion detection, which is imaged, on the display unit 13 via the controller 16.

As described above, according to the embodiment, time-series images are each divided into at least a lesion candidate area and a mucosa area that is positioned proximate to the lesion candidate area according to the feature data of a local area, and the similarity between the optical flows of each area between the time-series images can be determined. In addition to the feature data of the local areas in the images, the optical flows between the time-series images can be used to detect a lesion area. Accordingly, a lesion area that is difficult to detect using a single image can be detected accurately. Specifically, regarding images of contents, floating in the lumen, in time series, the movement of the mucosa and the movement of the contents may be different between the images. In contrast, it is assumed that a lesion on the mucosa moves similarly as the mucosa between the time-series images. According to the embodiment, a lesion candidate area whose movement is similar to that of the mucosa area among lesion candidate areas can be detected as a lesion area, which improves accuracy in detecting a lesion area.

The image processing apparatus according to the aspect of the invention can extract the abnormal candidate area as the abnormal area by dividing each image constituting the time-series images into category areas including the examined area and the abnormal candidate area and then judging the similarity of optical flows in each of the areas between images constituting the time-series images. Accordingly, an abnormal site in images constituting the time-series images can be detected accurately.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
a category area dividing unit that divides each image constituting time-series images of an object to be examined, which are captured in time series, into category areas including an examined area and an abnormal candidate area, the examined area showing the object to be examined, the abnormal candidate area being possibly an abnormal area showing an abnormal site of the object to be examined;
an optical flow calculator that calculates optical flows of the examined area and the abnormal candidate area from images constituting the time-series images; and
an abnormal area detector that compares the optical flow of the examined area and the optical flow of the abnormal candidate area, and detects the abnormal candidate area as the abnormal area according to the result of the comparison.

2. The image processing apparatus according to claim 1, wherein
the category area dividing unit includes
an image dividing unit that divides the image into a plurality of divided areas;
a feature data calculator that calculates feature data of each of the divided areas; and
an area classifying unit that classifies the divided areas into predetermined categories according to the feature data, and
the category area dividing unit divides the image into the category areas according to the result of the classification of the divided areas by the area classifying unit.

3. The image processing apparatus according to claim 2, wherein the image dividing unit includes an edge extracting unit that extracts an edge of the image and divides the image into the plurality of divided areas according to the edge.

4. The image processing apparatus according to claim 3, wherein the edge extracting unit extracts an edge of the color component corresponding to the absorption wavelength band of blood.

5. The image processing apparatus according to claim 1, wherein the optical flow calculator calculates, as the optical flow of the examined area, an optical flow of an examined area positioned proximate to the abnormal candidate area.

6. The image processing apparatus according to claim 1, wherein
the optical flow calculator includes
a structure area extracting unit that extracts a structure area from the image constituting the time-series images; and
a corresponding area extracting unit that extracts a corresponding area, which corresponds to the structure area, from an image that is captured at a time different from a time at which the image from which the structure area is extracted is captured, and
the optical flow calculator calculates the optical flows according to position information of the structure area and the corresponding area.

7. The image processing apparatus according to claim 1, wherein the abnormal area detector detects the abnormal candidate area as the abnormal area when the optical flow of the abnormal candidate area is similar to the optical flow of the examined area.

8. The image processing apparatus according to claim 7, wherein
the abnormal area detector includes
an abnormal candidate optical flow feature data calculator that calculates feature data of the optical flow of the abnormal candidate area; and
an examined optical flow feature data calculator that calculates feature data of the optical flow of the examined area positioned proximate to the abnormal candidate area, and
the abnormal area detector detects the abnormal candidate area as the abnormal area when a difference between the feature data of the optical flow of the abnormal candidate area and the feature data of the optical flow of the examined area is equal to or less than a predetermined value.

9. The image processing apparatus according to claim 8, wherein the feature data of the optical flows is calculated at least according to directions or magnitudes of the optical flows.

10. The image processing apparatus according to claim 1, wherein the time-series images are in-vivo images of a lumen.

11. The image processing apparatus according to claim 10, wherein the optical flow calculator calculates the optical flows using a color component corresponding to an absorption wavelength band of blood.

12. The image processing apparatus according to claim 1, wherein the examined area is a mucosa area.

13. An image processing program recording medium having stored thereon instructions that causes an image processing apparatus to perform:
a category area dividing procedure that divides each image constituting time-series images of an object to be examined, which are captured in time series, into category areas including an examined area and an abnormal candidate area, the examined area showing the object to be examined, the abnormal candidate area being possibly an abnormal area showing an abnormal site of the object to be examined;
an optical flow calculating procedure that calculates optical flows of the examined area and the abnormal candidate area from images constituting the time-series images; and
an abnormal area detecting procedure that compares the optical flow of the examined area and the optical flow of the abnormal candidate area, and detects the abnormal candidate area as the abnormal area according to the result of the comparison.

14. An image processing method comprising:
a category area dividing step that divides each image constituting time-series images of an object to be examined, which are captured in time series, into category areas including an examined area and an abnormal candidate area, the examined area showing the object to be examined, the abnormal candidate area being possibly an abnormal area showing an abnormal site of the object to be examined;
an optical flow calculating step that calculates optical flows of the examined area and the abnormal candidate area from images constituting the time-series images; and
an abnormal area detecting step that compares the optical flow of the examined area and the optical flow of the abnormal candidate area, and detects the abnormal candidate area as the abnormal area according to the result of the comparison.

* * * * *